US012649711B2

(12) United States Patent
Ma et al.

(10) Patent No.: US 12,649,711 B2
(45) Date of Patent: Jun. 9, 2026

(54) METHOD FOR CO-PRODUCTION OF CARBOXYLIC ACID AND EPSILON-CAPROLACTONE BASED ON AEROBIC OXIDATION

(71) Applicant: ZHEJIANG UNIVERSITY, Zhejiang (CN)

(72) Inventors: Shengming Ma, Zhejiang (CN); Jinxian Liu, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 941 days.

(21) Appl. No.: 17/641,585

(22) PCT Filed: Jul. 21, 2020

(86) PCT No.: PCT/CN2020/103204
§ 371 (c)(1),
(2) Date: Mar. 9, 2022

(87) PCT Pub. No.: WO2021/047292
PCT Pub. Date: Mar. 18, 2021

(65) Prior Publication Data

US 2022/0298096 A1 Sep. 22, 2022

(30) Foreign Application Priority Data

Sep. 12, 2019 (CN) ........................ 201910864678.7

(51) Int. Cl.
*C07C 51/235* (2006.01)
*C07D 313/04* (2006.01)

(52) U.S. Cl.
CPC .......... *C07C 51/235* (2013.01); *C07D 313/04* (2013.01)

(58) Field of Classification Search
CPC ............................ C07C 51/235; C07D 313/04
See application file for complete search history.

(56) References Cited

U.S. PATENT DOCUMENTS 5,278,321 A 1/1994 Tanaka et al.

FOREIGN PATENT DOCUMENTS

| | | |
|---|---|---|
| CN | 104592192 A | 5/2015 |
| CN | 105237507 A | 1/2016 |
| CN | 107176899 A | 9/2017 |

OTHER PUBLICATIONS

CN104592192A (Sun et al. English language machine translation) (Year: 2015).*
J. Am. Chem. Soc. 2016, 138, 8344-8347 (Jiang et al.) (Year: 2016).*
Practical Process Research and Development (Anderson) (Year: 2000).*
International Search Report, issued in PCT/CN2020/103204, dated Aug. 31, 2020.
Written Opinion of the International Searching Authority, issued in PCT/CN2020/103204, dated Aug. 31, 2020.

* cited by examiner

*Primary Examiner* — Amy C Bonaparte
*Assistant Examiner* — Derek Rhoades
(74) *Attorney, Agent, or Firm* — Birch, Stewart, Kolasch & Birch, LLP

(57) ABSTRACT

The present invention discloses a newly high-efficiency method for co-production of carboxylic acid and ε-caprolactone based on the aerobic oxidation, that is, under the developed catalytic system, the aldehyde is oxidized to corresponding carboxylic acid while cyclohexanone is oxidized to ε-caprolactone, realizes the co-production of carboxylic acid and ε-caprolactone. The salient features of this method include the use of cheap and readily available substrates, mild reaction conditions, environmentally friendly, and easy operation. It can realize the co-production of carboxylic acid and high value-added ε-caprolactone.

6 Claims, No Drawings

METHOD FOR CO-PRODUCTION OF CARBOXYLIC ACID AND EPSILON-CAPROLACTONE BASED ON AEROBIC OXIDATION

TECHNICAL FIELD

The present invention belongs to the field of chemical synthesis, relates to a method for co-production of carboxylic acid and ε-caprolactone based on aerobic oxidation.

BACKGROUND OF THE INVENTION

ε-caprolactone is an important chemical raw material, and its polymers are widely used in biodegradable plastics, medical polymer materials, adhesives, coatings and other fields. At present, the production of ε-caprolactone can adopt either the cyclohexanone route or the non-cyclohexanone route. Industrially, ε-caprolactone is produced mainly by Baeyer-Villiger oxidation of cyclohexanone (Baeyer, A.; Villiger, V. *Ber.* 1899, 32, 3625; Krow, G. R. *Org. React.* 1993, 43, 251; Renz, M.; Meunier, B. *Eur. J. Org. Chem.* 1999, 4, 737). Organic peracids (such as peracetic acid, m-CPBA, etc.) are the most commonly used oxidants in Baeyer-Villiger oxidation (path a: such as *J. Am. Chem. Soc.,* 1958, 80, 4079*; Org. Lett.,* 2005, 7, 5015*; Synth. Commun.,* 1989, 19, 829*; J. Mol. Catal. A: Chem.,* 2004, 212, 237*; Angew. Chem. Int. Ed.,* 2015, 54, 11848), but due to the few types of peroxy acids on the market, inconvenient storage, harsh operating conditions and high price, this route is not practical (U.S. Pat. No. 6,531,615 B2), and the mature process is monopolized by the United States, Britain, Japan and other countries. The domestic market supply is still dominated by imports (*Synthetic Fiber Industry,* 2016, 24, 42).

Due to the high cost and potential safety hazard of the direct organic peroxy acid method, it has been gradually replaced by the oxidation method based on hydrogen peroxide in recent years (path b: *Angew. Chem., Int. Ed.,* 1998, 37, 1198*; Org. Lett.,* 2000, 2, 2861*; Nature,* 2001, 412, 423*; Angew. Chem. Int. Ed.,* 2002, 41, 4481*; Angew. Chem. Int. Ed.,* 2012, 51, 11736*; ACS Catal.,* 2013, 3, 513). Although the hydrogen peroxide method has the advantages of being safer, more economical and more environmentally friendly than the organic peracid method, there are also several significant problems: one is that the activity of hydrogen peroxide is lower than that of the organic peracid described in path a., so an efficient and stable catalyst is needed to activate it in the reaction; the second is that the presence of water in the reaction process may cause the hydrolysis of the ester; the third is that the miscibility of high-concentration hydrogen peroxide and organic solvents also has safety problems (*Chem. Rev.,* 2004, 104, 4105*; Advances in Chemical Engineering,* 2017, 36, 1424). Therefore, the indirect method (path c) based on air oxidation has received more and more attention.

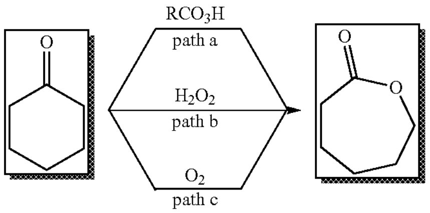

Carboxylic acid is also a kind of basic chemical raw material, which is mainly produced by oxidation reaction in industry. Taking into account factors such as cost and environmental protection, the production process of carboxylic acid based on air oxidation has attracted more and more attention in the industry due to its advantages of low price, cleanliness and high efficiency (*Chem. Lett.,* 1991, 641*; J. Org. Chem.,* 1994, 59, 2915*; ACS Catal.,* 2013, 3, 230*; Chem. Eur. J.,* 2017, 23, 9831). In recent years, our group has developed a carboxylic acid synthesis technology based on cheap metal catalysis (*J. Am. Chem. Soc.,* 2016, 138, 8344*; Synthesis,* 2018, 50, 1629*; Chin. J Chem.,* 2018, 36, 15.).

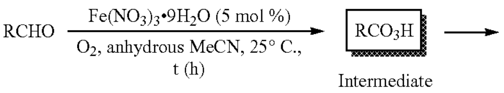

*Chin. J. Chem.,* 2018, 36, 15-19

SUMMARY OF THE INVENTION

In order to overcome the above-mentioned defects of the prior art, the present invention studies and develops a newly high-efficiency method for co-production of carboxylic acid and ε-caprolactone based on the catalytic aerobic oxidation.

The present invention aims to provide a simple, efficient, fast and more economical method based on the presence of catalyst and oxygen to realize the Baeyer-Villiger oxidation of cyclohexanone to produce ε-caprolactone while oxidizing aldehydes to corresponding carboxylic acids. Its reaction equation is shown in the following equation (A):

reaction equation (A)

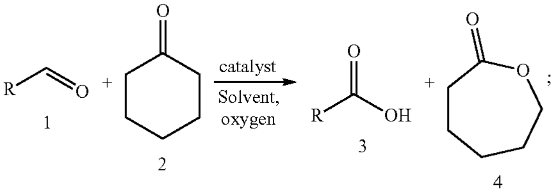

1 2 3 4 wherein, R is a C2-C11 linear or branched alkyl or aryl group.

preferably, R is a C2-C4 linear or branched alkyl or phenyl.

The method comprises the following steps: catalyst, organic solvent and cyclohexanone are added to a three-necked flask, after replacing the air with oxygen for three times, the aldehyde solution is added slowly. The resulting mixture is stirred until the completion of the reaction, then the ε-caprolactone and carboxylic acid can be obtained by column chromatography or distillation.

The principle of the present invention is that the aldehyde is oxidized to the corresponding peroxy acid under the action of the catalyst, reacts with cyclohexanone to generate Criegee intermediate, and then undergoes rearrangement reaction, thereby realizing the co-production of carboxylic acid (product 1) and ε-caprolactone (product 2), as shown in formula (B):

formula (B)

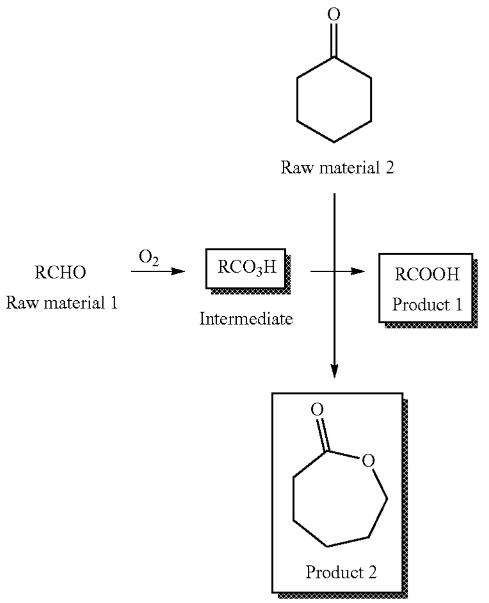

In the present invention, the said catalyst is a nitrate, selected from one or more of ferric nitrate nonahydrate and copper nitrate trihydrate, etc.; preferably, is ferric nitrate nonahydrate.

In the present invention, the molar ratio of the said aldehyde, cyclohexanone and catalyst is 150~300:100:1~10; preferably, is 250:100:2.5.

In the present invention, the said catalyst further comprises 2,2,6,6-tetramethylpiperidine oxide.

In the present invention, the molar ratio of the said cyclohexanone and 2,2,6,6-tetramethylpiperidine oxide is 100:1~5; preferably, is 100:1.

In the present invention, the said organic solvent is selected from one or more of 1,2-dichloroethane, 1,1-dichloroethane, 1,2-dichloropropane, 1,3-dichloropropane and ethyl acetate, etc.; preferably, is 1,2-dichloroethane.

In the present invention, the said oxygen is pure oxygen or oxygen in the air.

In the present invention, the said reaction temperature is from room temperature to 50° C.; preferably, is 30° C.

In the present invention, the said reaction time is 4-72 hours; preferably, is 24 hours.

In the present invention, the addition method is one-time addition or dropwise addition slowly; preferably, the solution of aldehyde (raw material 1) is slowly added dropwise to the solution of cyclohexanone (raw material 2), and the dropwise addition is completed in 5 hours.

The present invention overcomes the disadvantages of the traditional method and has the following advantages: 1) only a simple catalyst is required; 2) the atom economy is high; 3) in-situ conversion of generated peroxy acid in the process; 4) the reaction conditions are mild and easy for operation; 5) environmentally friendly.

The innovation of the present invention lies in the development of a new technology for the co-production of carboxylic acid and ε-caprolactone based on the catalytic aerobic oxidation under mild conditions.

PREFERRED EMBODIMENTS OF THE INVENTION

The invention will be further described in detail in combination with the following specific embodiments. The protection content of the invention is not limited to the following embodiments.

Without departing from the spirit and scope of the invention, the changes and advantages that can be thought of by those skilled in the art are included in the invention, and the scope of protection is based on the appended claims.

Example 1

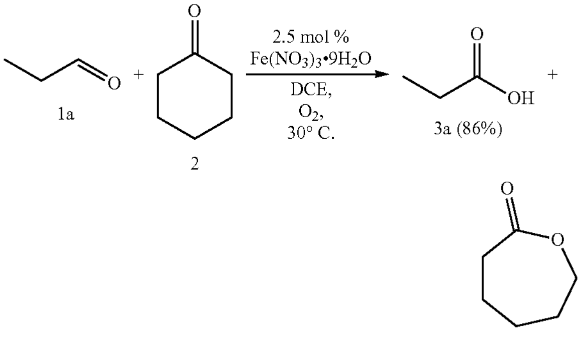

1a + 2 → 3a (86%) + 4 (72%)

(Typical procedure) Ferric nitrate nonahydrate (101.9 mg, 0.25 mmol), 1,2-dichloroethane (20 mL) and cyclohexanone (980.2 mg, 10.0 mmol) were added into a three-neck bottle, after replacing the air with oxygen for three times, the propionaldehyde (1.4541 g, 25 mmol) solution in 1,2-dichloroethane (50 mL) was added dropwise at 30° C. over 5 hours. The resulting mixture was stirred at 30° C. until the completion of the reaction. 86% of 3a (with dibromomethane as internal standard, NMR yield) and 72% of 4 (with dibromomethane as internal standard, NMR yield) were obtained.

Example 2

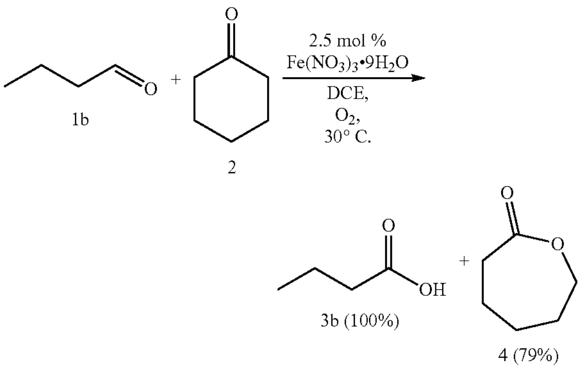

1b + 2 → 3b (100%) + 4 (79%)

Ferric nitrate nonahydrate (100.4 mg, 0.25 mmol), 1,2-dichloroethane (20 mL) and cyclohexanone (980.7 mg, 10.0 mmol) were added into a three-neck bottle, after replacing the air with oxygen for three times, the n-butyraldehyde (1.8045 g, 25 mmol) solution in 1,2-dichloroethane (50 mL) was added dropwise at 30° C. over 5 hours. The resulting mixture was stirred at 30° C. until the completion of the reaction. 100% of 3b (with dibromomethane as internal standard, NMR yield) and 79% of 4 (with dibromomethane as internal standard, NMR yield) were obtained.

Example 3

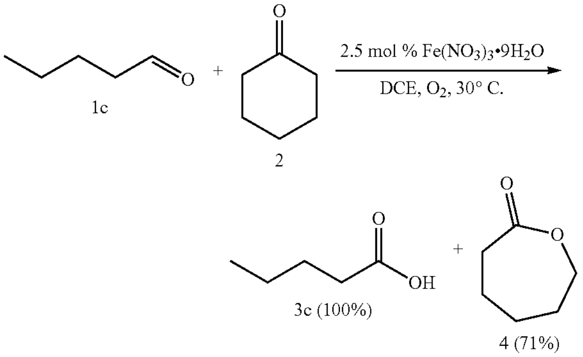

1c 2 3c (100%) 4 (71%)

Ferric nitrate nonahydrate (100.0 mg, 0.25 mmol), 1,2-dichloroethane (20 mL) and cyclohexanone (981.5 mg, 10.0 mmol) were added into a three-neck bottle, after replacing the air with oxygen for three times, the n-valeraldehyde (2.1446 g, 25 mmol) solution in 1,2-dichloroethane (50 mL) was added dropwise at 30° C. over 5 hours. The resulting mixture was stirred at 30° C. until the completion of the reaction. 100% of 3c (with dibromomethane as internal standard, NMR yield) and 71% of 4 (with dibromomethane as internal standard, NMR yield) were obtained.

Example 4

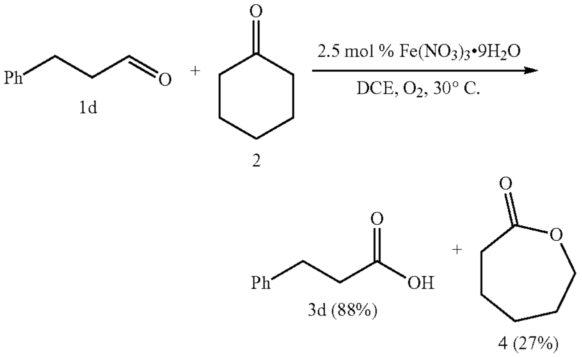

1d 2 3d (88%) 4 (27%)

Ferric nitrate nonahydrate (101.0 mg, 0.25 mmol), 1,2-dichloroethane (20 mL) and cyclohexanone (980.6 mg, 10.0 mmol) were added into a three-neck bottle, after replacing the air with oxygen for three times, the benzenepropanal (3.3604 g, 25 mmol) solution in 1,2-dichloroethane (50 mL) was added dropwise at 30° C. over 5 hours. The resulting mixture was stirred at 30° C. until the completion of the reaction. 88% of 3d (with dibromomethane as internal standard, NMR yield) and 27% of 4 (with dibromomethane as internal standard, NMR yield) were obtained.

Example 5

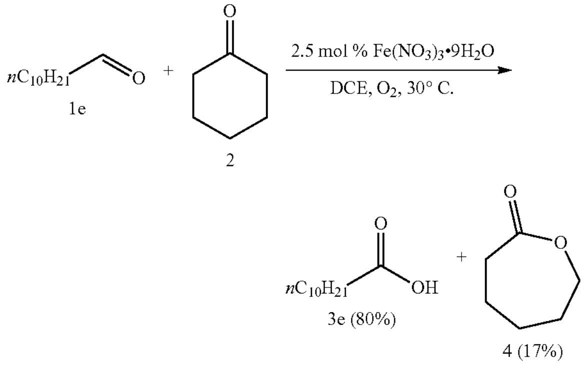

1e 2 3e (80%) 4 (17%)

Ferric nitrate nonahydrate (100.0 mg, 0.25 mmol), 1,2-dichloroethane (20 mL) and cyclohexanone (980.0 mg, 10.0 mmol) were added into a three-neck bottle, after replacing the air with oxygen for three times, the n-undecanal (4.3117 g, 25 mmol) solution in 1,2-dichloroethane (50 mL) was added dropwise at 30° C. over 5 hours. The resulting mixture was stirred at 30° C. until the completion of the reaction. 80% of 3e (with dibromomethane as internal standard, NMR yield) and 17% of 4 (with dibromomethane as internal standard, NMR yield) were obtained.

Example 6

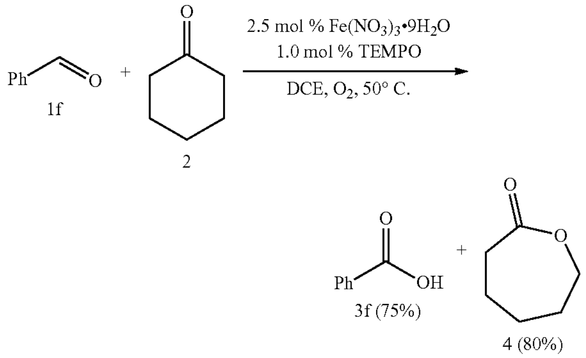

1f 2 3f (75%) 4 (80%)

Ferric nitrate nonahydrate (9.7 mg, 0.025 mmol), TEMPO (1.5 mg, 0.01 mmol), 1,2-dichloroethane (4 mL), cyclohexanone (98.2 mg, 1.0 mmol) and benzaldehyde (321.0 mg, 3.0 mmol) were added into a reaction tube, after replacing the air with oxygen for three times, the resulting mixture was stirred at 50° C. for 24 hours. 75% of 3f (with dibromomethane as internal standard, NMR yield) and 4 (NMR 72%; isolated yield, 64.0 mg, 56%) were obtained.

ε-caprolactone (4): $^1H$ NMR (300 MHz, $CDCl_3$): δ 4.25-4.20 (m, 2H, $OCH_2$), 2.68-2.60 (m, 2H, $COCH_2$), 1.91-1.70 (m, 6H, $CH_2$×3); $^{13}C$ NMR (75 MHz, $CDCl_3$) δ 176.1, 69.0, 34.2, 29.0, 28.6, 22.6; IR (neat) ν ($cm^{-1}$)=3588, 2935, 2863, 1733, 1477, 1438, 1393, 1348, 1328, 1292, 1252, 1226, 1168, 1100, 1088, 1055, 1015; MS (EI): m/z (%) 114 ($M^+$, 15.38), 55 (100).

Example 7

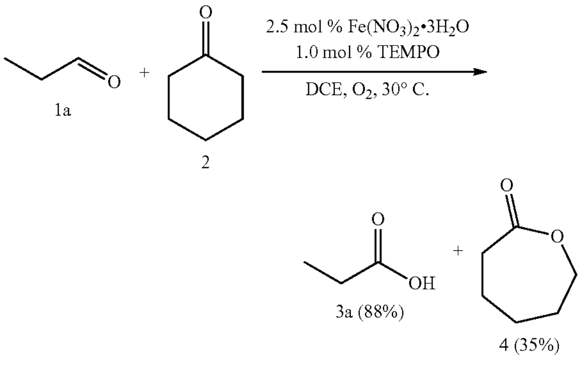

Copper nitrate trihydrate (59.6 mg, 0.25 mmol), 1,2-dichloroethane (20 mL) and cyclohexanone (982.4 mg, 10.0 mmol) were added into a three-neck bottle, after replacing the air with oxygen for three times, the propionaldehyde (1.4458 g, 25 mmol) solution in 1,2-dichloroethane (50 mL) was added dropwise at 30° C. over 5 hours. The resulting mixture was stirred at 30° C. until the completion of the reaction. 88% of 3a (with dibromomethane as internal standard, NMR yield) and 35% of 4 (with dibromomethane as internal standard, NMR yield) were obtained.

Example 8

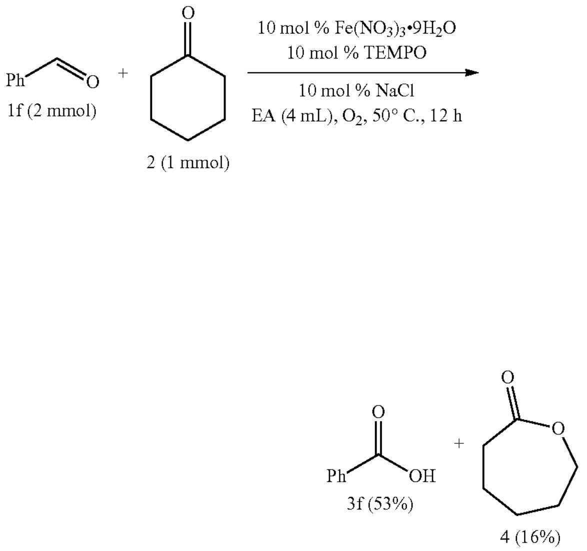

Ferric nitrate nonahydrate (40.1 mg, 0.1 mmol), TEMPO (15.8 mg, 0.1 mmol), sodium chloride (5.9 mg, 0.1 mmol), ethyl acetate (4 mL), cyclohexanone (97.8 mg, 1.0 mmol) and benzaldehyde (213.2 mg, 2.0 mmol) were added into a three-neck bottle, after replacing the air with oxygen for three times, the resulting mixture was stirred at 50° C. for 12 hours. 53% of 3f (with dibromomethane as internal standard, NMR yield) and 16% of 4 (with dibromomethane as internal standard, NMR yield) were obtained.

Example 9

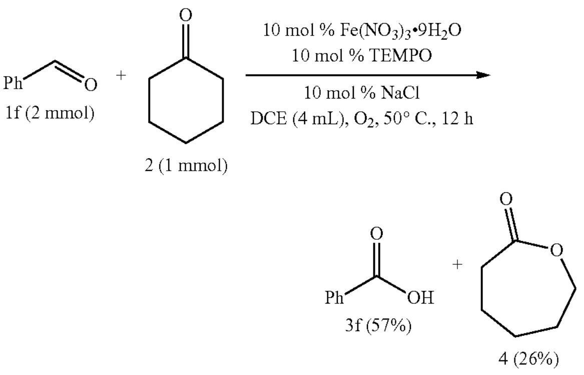

Ferric nitrate nonahydrate (40.0 mg, 0.1 mmol), TEMPO (15.5 mg, 0.1 mmol), sodium chloride (5.4 mg, 0.1 mmol), 1,2-dichloroethane (4 mL), cyclohexanone (97.8 mg, 1.0 mmol) and benzaldehyde (213.1 mg, 2.0 mmol) were added into a three-neck bottle, after replacing the air with oxygen for three times, the resulting mixture was stirred at 50° C. for 12 hours. 57% of 3f (with dibromomethane as internal standard, NMR yield) and 26% of 4 (with dibromomethane as internal standard, NMR yield) were obtained.

Example 10

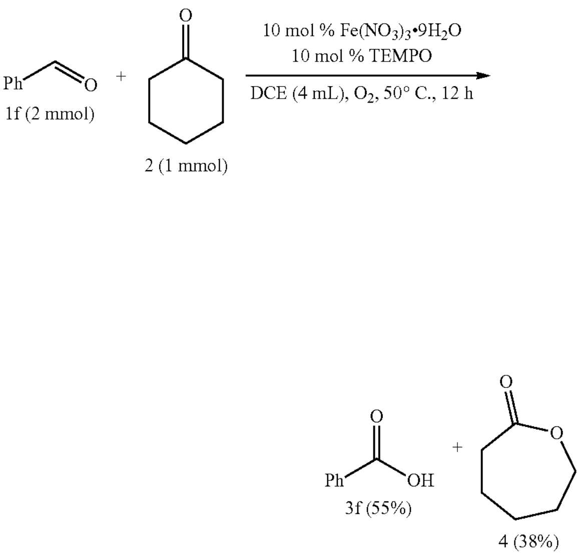

Ferric nitrate nonahydrate (40.3 mg, 0.1 mmol), TEMPO (15.2 mg, 0.1 mmol), 1,2-dichloroethane (4 mL), cyclohexanone (99.3 mg, 1.0 mmol) and benzaldehyde (214.2 mg, 2.0 mmol) were added into a three-neck bottle, after replacing the air with oxygen for three times, the resulting mixture was stirred at 50° C. for 12 hours. 55% of 3f (with dibromomethane as internal standard, NMR yield) and 38% of 4 (with dibromomethane as internal standard, NMR yield) were obtained.

Example 11

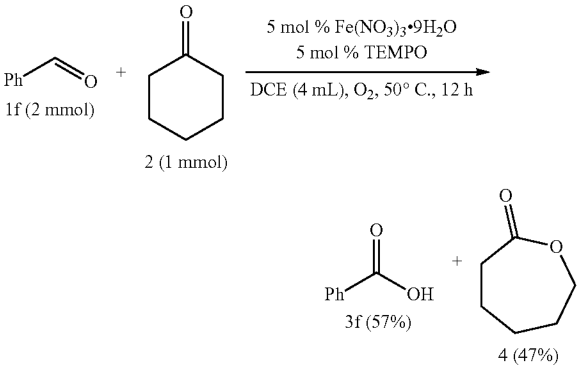

Ferric nitrate nonahydrate (21.0 mg, 0.05 mmol), TEMPO (7.9 mg, 0.05 mmol), 1,2-dichloroethane (4 mL), cyclohexanone (99.3 mg, 1.0 mmol) and benzaldehyde (211.6 mg, 2.0 mmol) were added into a three-neck bottle, after replacing the air with oxygen for three times, the resulting mixture was stirred at 50° C. for 12 hours. 57% of 3f (with dibromomethane as internal standard, NMR yield) and 47% of 4 (with dibromomethane as internal standard, NMR yield) were obtained.

Example 12

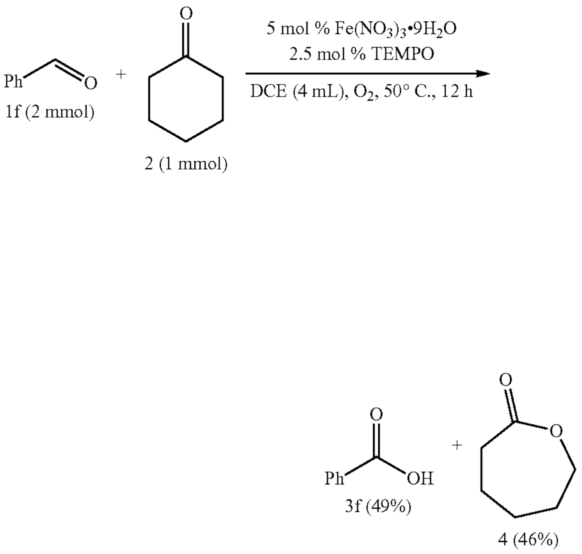

Ferric nitrate nonahydrate (21.0 mg, 0.05 mmol), TEMPO (3.7 mg, 0.025 mmol), 1,2-dichloroethane (4 mL), cyclohexanone (97.1 mg, 1.0 mmol) and benzaldehyde (212.0 mg, 2.0 mmol) were added into a three-neck bottle, after replacing the air with oxygen for three times, the resulting mixture was stirred at 50° C. for 12 hours. 49% of 3f (with dibromomethane as internal standard, NMR yield) and 46% of 4 (with dibromomethane as internal standard, NMR yield) were obtained.

Example 13

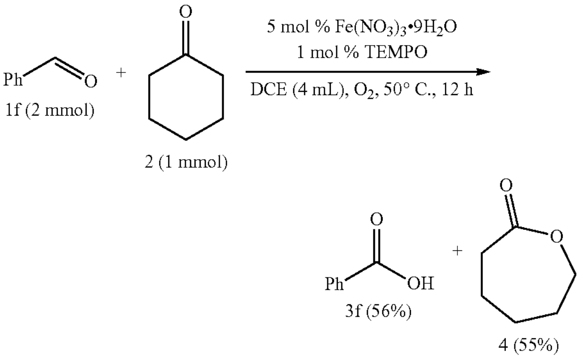

Ferric nitrate nonahydrate (19.7 mg, 0.05 mmol), TEMPO (1.7 mg, 0.01 mmol), 1,2-dichloroethane (4 mL), cyclohexanone (99.9 mg, 1.0 mmol) and benzaldehyde (212.7 mg, 2.0 mmol) were added into a three-neck bottle, after replacing the air with oxygen for three times, the resulting mixture was stirred at 50° C. for 12 hours. 56% of 3f (with dibromomethane as internal standard, NMR yield) and 55% of 4 (with dibromomethane as internal standard, NMR yield) were obtained.

Example 14

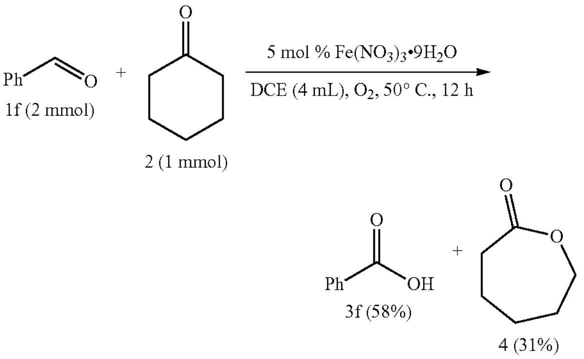

Ferric nitrate nonahydrate (21.2 mg, 0.05 mmol), 1,2-dichloroethane (4 mL), cyclohexanone (99.4 mg, 1.0 mmol) and benzaldehyde (215.9 mg, 2.0 mmol) were added into a three-neck bottle, after replacing the air with oxygen for three times, the resulting mixture was stirred at 50° C. for 12 hours. 58% of 3f (with dibromomethane as internal standard, NMR yield) and 31% of 4 (with dibromomethane as internal standard, NMR yield) were obtained.

Example 15

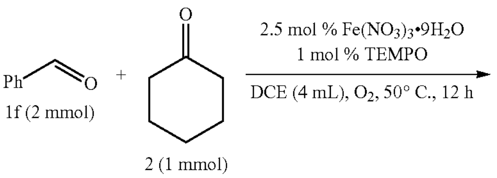

-continued

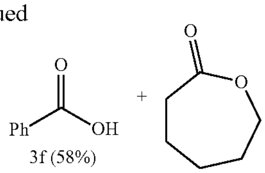

3f (58%)

4 (58%)

Ferric nitrate nonahydrate (11.2 mg, 0.025 mmol), TEMPO (1.7 mg, 0.01 mmol), 1,2-dichloroethane (4 mL), cyclohexanone (99.6 mg, 1.0 mmol) and benzaldehyde (215.5 mg, 2.0 mmol) were added into a three-neck bottle, after replacing the air with oxygen for three times, the resulting mixture was stirred at 50° C. for 12 hours. 58% of 3f (with dibromomethane as internal standard, NMR yield) and 58% of 4 (with dibromomethane as internal standard, NMR yield) were obtained.

Example 16

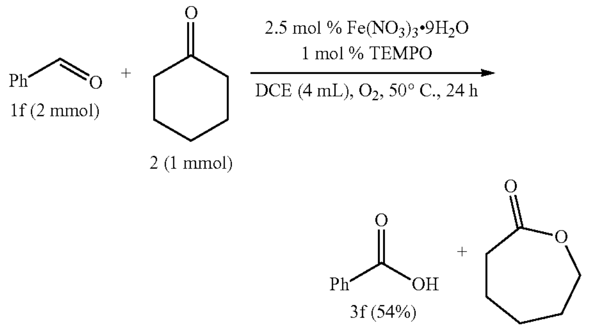

1f (2 mmol)

2 (1 mmol)

3f (54%)

4 (65%)

Ferric nitrate nonahydrate (9.8 mg, 0.025 mmol), TEMPO (1.9 mg, 0.01 mmol), 1,2-dichloroethane (4 mL), cyclohexanone (97.7 mg, 1.0 mmol) and benzaldehyde (215.6 mg, 2.0 mmol) were added into a three-neck bottle, after replacing the air with oxygen for three times, the resulting mixture was stirred at 50° C. for 24 hours. 54% of 3f (with dibromomethane as internal standard, NMR yield) and 65% of 4 (with dibromomethane as internal standard, NMR yield) were obtained.

Example 17

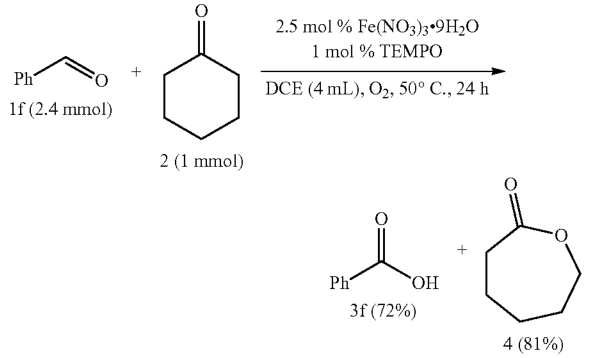

1f (2.4 mmol)

2 (1 mmol)

3f (72%)

4 (81%)

Ferric nitrate nonahydrate (10.5 mg, 0.025 mmol), TEMPO (1.8 mg, 0.01 mmol), 1,2-dichloroethane (4 mL), cyclohexanone (98.9 mg, 1.0 mmol) and benzaldehyde (250.0 mg, 2.4 mmol) were added into a three-neck bottle, after replacing the air with oxygen for three times, the resulting mixture was stirred at 50° C. for 24 hours. 72% of 3f (with dibromomethane as internal standard, NMR yield) and 81% of 4 (with dibromomethane as internal standard, NMR yield) were obtained.

Example 18

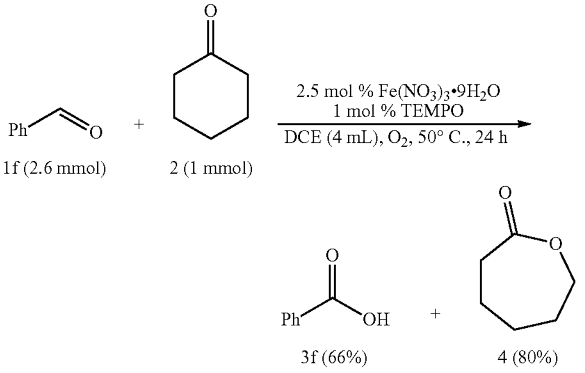

1f (2.6 mmol)

2 (1 mmol)

3f (66%)

4 (80%)

Ferric nitrate nonahydrate (10.5 mg, 0.025 mmol), TEMPO (1.7 mg, 0.01 mmol), 1,2-dichloroethane (4 mL), cyclohexanone (97.9 mg, 1.0 mmol) and benzaldehyde (271.3 mg, 2.6 mmol) were added into a three-neck bottle, after replacing the air with oxygen for three times, the resulting mixture was stirred at 50° C. for 24 hours. 66% of 3f (with dibromomethane as internal standard, NMR yield) and 80% of 4 (with dibromomethane as internal standard, NMR yield) were obtained.

Example 19

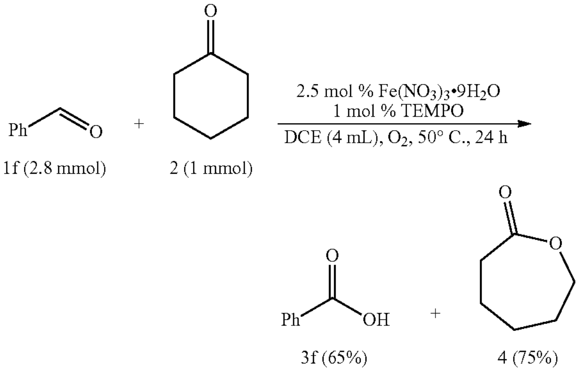

1f (2.8 mmol)

2 (1 mmol)

3f (65%)

4 (75%)

Ferric nitrate nonahydrate (10.3 mg, 0.025 mmol), TEMPO (1.7 mg, 0.01 mmol), 1,2-dichloroethane (4 mL), cyclohexanone (97.6 mg, 1.0 mmol) and benzaldehyde (299.9 mg, 2.8 mmol) were added into a three-neck bottle, after replacing the air with oxygen for three times, the resulting mixture was stirred at 50° C. for 24 hours. 65% of 3f (with dibromomethane as internal standard, NMR yield) and 75% of 4 (with dibromomethane as internal standard, NMR yield) were obtained.

Example 20

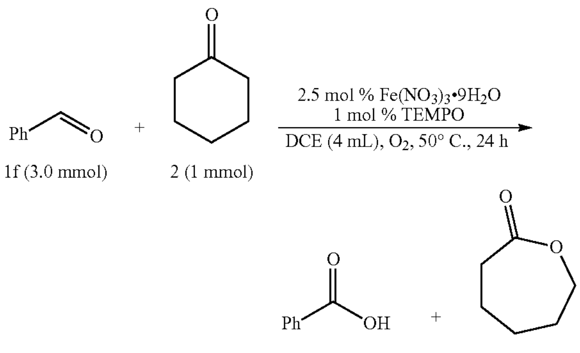

1f (3.0 mmol) 2 (1 mmol)

3f (62%) 4 (80%)

Ferric nitrate nonahydrate (9.7 mg, 0.025 mmol), TEMPO (1.5 mg, 0.01 mmol), 1,2-dichloroethane (4 mL), cyclohexanone (98.2 mg, 1.0 mmol) and benzaldehyde (321.0 mg, 2.8 mmol) were added into a three-neck bottle, after replacing the air with oxygen for three times, the resulting mixture was stirred at 50° C. for 24 hours. 62% of 3f (with dibromomethane as internal standard, NMR yield) and 80% of 4 (with dibromomethane as internal standard, NMR yield) were obtained.

Example 21

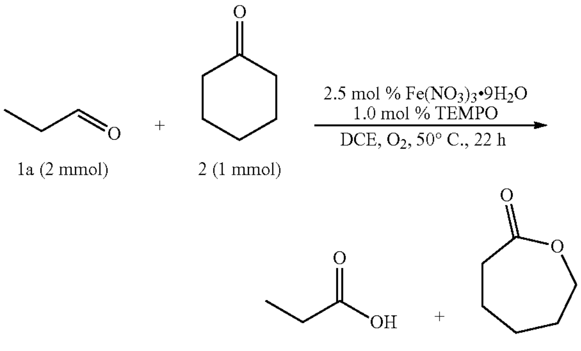

1a (2 mmol) 2 (1 mmol)

3a (43%) 4 (19%)

Ferric nitrate nonahydrate (10.2 mg, 0.025 mmol), TEMPO (1.7 mg, 0.01 mmol), 1,2-dichloroethane (20 mL), cyclohexanone (98.1 mg, 1.0 mmol) and propionaldehyde (113.0 mg, 2.0 mmol) were added into a three-neck bottle, after replacing the air with oxygen for three times, the resulting mixture was stirred at 50° C. for 22 hours. 43% of 3a (with dibromomethane as internal standard, NMR yield) and 19% of 4 (with dibromomethane as internal standard, NMR yield) were obtained.

Example 22

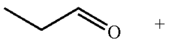

(dropping)
1a (2 mmol)

-continued

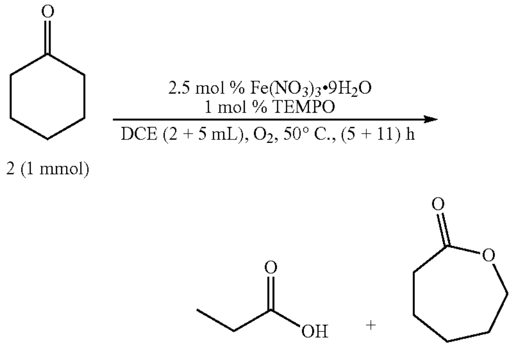

2 (1 mmol)

3a (92%) 4 (57%)

Ferric nitrate nonahydrate (10.3 mg, 0.025 mmol), TEMPO (1.5 mg, 0.01 mmol), 1,2-dichloroethane (2 mL) and cyclohexanone (98.1 mg, 1.0 mmol) were added into a three-neck bottle, after replacing the air with oxygen for three times, the propionaldehyde (114.0 mg, 2.0 mmol) solution in 1,2-dichloroethane (5 mL) was added dropwise at 50° C. over 5 hours. The resulting mixture was stirred at 50° C. until the completion of the reaction. 92% of 3a (with dibromomethane as internal standard, NMR yield) and 57% of 4 (with dibromomethane as internal standard, NMR yield) were obtained.

Example 23

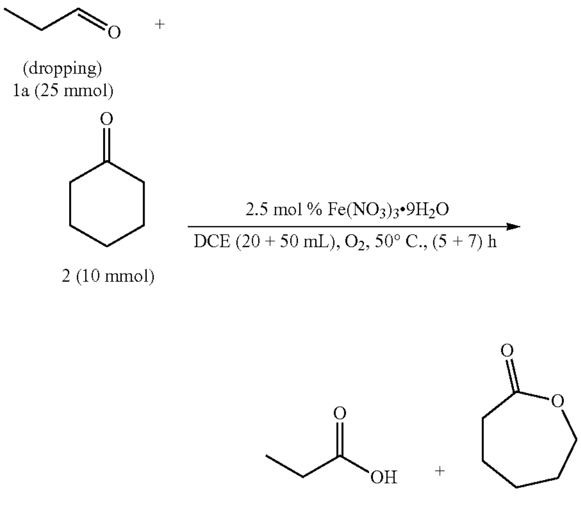

(dropping)
1a (25 mmol)

2 (10 mmol)

3a (92%) 4 (77%)

Ferric nitrate nonahydrate (101.4 mg, 0.25 mmol), 1,2-dichloroethane (20 mL) and cyclohexanone (991.9 mg, 10.0 mmol) were added into a three-neck bottle, after replacing the air with oxygen for three times, the propionaldehyde (1.4574 g, 25.0 mmol) solution in 1,2-dichloroethane (50 mL) was added dropwise at 50° C. over 5 hours. The resulting mixture was stirred at 50° C. until the completion of the reaction. 92% of 3a (with dibromomethane as internal standard, NMR yield) and 77% of 4 (with dibromomethane as internal standard, NMR yield) were obtained.

Example 24

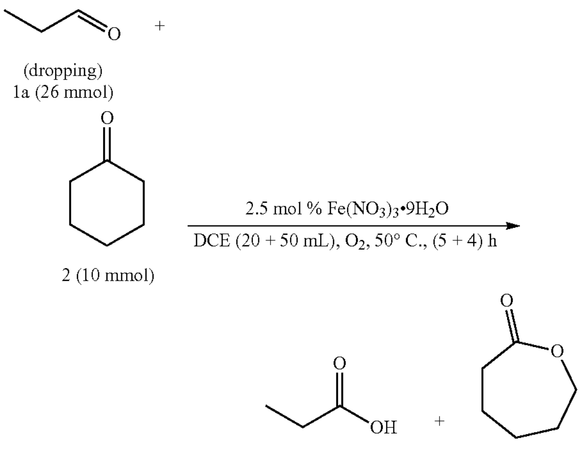

(dropping) 1a (26 mmol) + 2 (10 mmol)

3a (81%) + 4 (73%)

Ferric nitrate nonahydrate (100.9 mg, 0.25 mmol), 1,2-dichloroethane (20 mL) and cyclohexanone (980.0 mg, 10.0 mmol) were added into a three-neck bottle, after replacing the air with oxygen for three times, the propionaldehyde (1.5138 g, 26.0 mmol) solution in 1,2-dichloroethane (50 mL) was added dropwise at 50° C. over 5 hours. The resulting mixture was stirred at 50° C. until the completion of the reaction. 81% of 3a (with dibromomethane as internal standard, NMR yield) and 73% of 4 (with dibromomethane as internal standard, NMR yield) were obtained.

Example 25

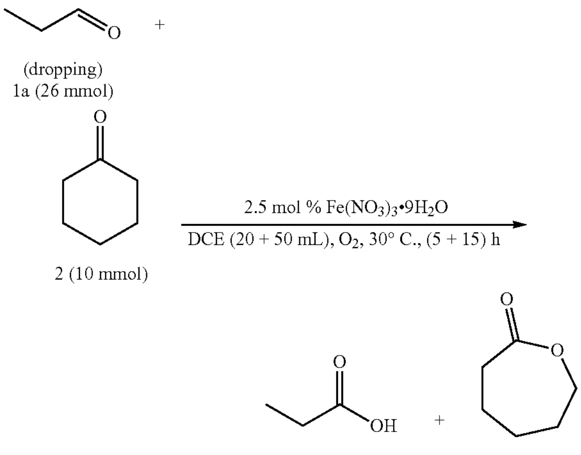

(dropping) 1a (26 mmol) + 2 (10 mmol)

3a (76%) + 4 (71%)

Ferric nitrate nonahydrate (101.3 mg, 0.25 mmol), 1,2-dichloroethane (20 mL) and cyclohexanone (980.7 mg, 10.0 mmol) were added into a three-neck bottle, after replacing the air with oxygen for three times, the propionaldehyde (1.5224 g, 26.0 mmol) solution in 1,2-dichloroethane (50 mL) was added dropwise at 30° C. over 5 hours. The resulting mixture was stirred at 30° C. until the completion of the reaction. 3a 76% (with dibromomethane as internal standard, NMR yield) and 4 71% (with dibromomethane as internal standard, NMR yield) were obtained.

The corresponding beneficial effects of the present invention are analyzed by specific embodiments:

1) The effect of solvent on this reaction: benzaldehyde (1f) and cyclohexanone (2) were used as reaction substrates, and 10 mol % ferric nitrate nonahydrate, 2,2,6,6-tetramethylpiperidine oxide, sodium chloride as catalyst, reacted in different solvents for 12 hours (serial number 1-10), see Table 1; when the solvent was 1,2-dichloroethane, the yield of benzoic acid (3f) was 57% and the yield of ε-caprolactone (4) was 26% (Example 9).

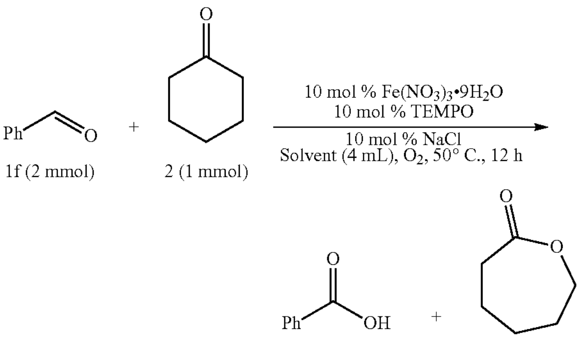

1f (2 mmol) + 2 (1 mmol)

3f + 4

TABLE 1

| Serial number | solvent | benzoic acid 3f (%, NMR yield) | ε-caprolactone 4 (%, NMR yield) |
|---|---|---|---|
| 1 | Toluene | 2 | 0 |
| 2 | Dichloromethane | 1 | 0 |
| 3 | Chloroform | 2 | 0 |
| 4 | Acetic acid | 14 | 0 |
| 5 | Acetonitrile | 17 | 0 |
| 6 | Tetrahydrofuran | 28 | 0 |
| 7 | Methanol | 9 | 0 |
| 8 | Ether | 2 | 0 |
| 9 | Ethyl acetate | 53 | 16 |
| 10 | 1,2-dichloroethane | 57 | 26 |

2) The influence of catalyst change on the reaction: change the composition of the catalyst (see Table 2), and find that the yield of caprolactone is improved without adding sodium chloride (serial number 2, Example 10); when the catalyst dosage is composed of 2.5 mol % of ferric nitrate nonahydrate and 1 mol % of 2,2,6,6-tetramethylpiperidine oxide, benzoic acid and ε-caprolactone were obtained in 58% yield respectively (serial number. 7, Example 15).

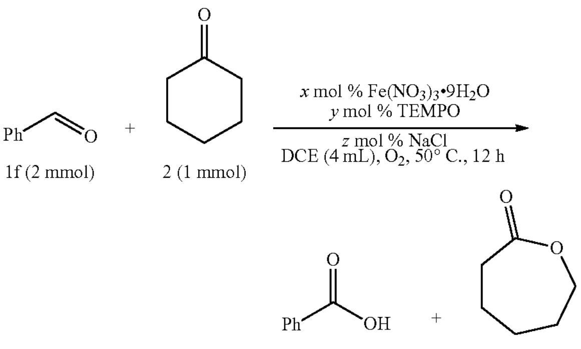

1f (2 mmol) + 2 (1 mmol)

3f + 4

TABLE 2

| Serial number | x | y | z | benzoic acid 3f (%, NMR yield) | ε-caprolactone 4 (%, NMR yield) |
|---|---|---|---|---|---|
| 1 | 10 | 10 | 10 | 57 | 26 |
| 2 | 10 | 10 | 0 | 55 | 38 |
| 3 | 5 | 5 | 0 | 57 | 47 |
| 4 | 5 | 2.5 | 0 | 49 | 46 |
| 5 | 5 | 1 | 0 | 56 | 55 |
| 6 | 5 | 0 | 0 | 58 | 31 |
| 7 | 2.5 | 1 | 0 | 58 | 58 |

3) The influence of the change of the added amount of benzaldehyde on the reaction: increasing the equivalent of benzaldehyde will help to increase the yield of caprolactone (see Table 3); when the amount of benzaldehyde is 2.4 equivalents, benzoic acid and ε-caprolactone were obtained in 72% and 810% yield respectively (serial number. 2, Example 17).

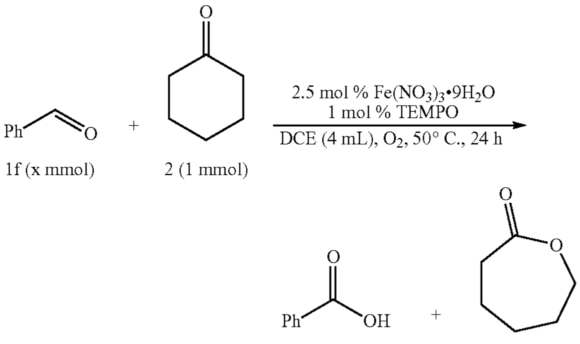

1f (x mmol) 2 (1 mmol)
3f 4

TABLE 3

| Serial number | x | benzoic acid 3f (%, NMR yield) | ε-caprolactone 4 (%, NMR yield) |
|---|---|---|---|
| 1 | 2.0 | 54 | 65 |
| 2 | 2.4 | 72 | 81 |
| 3 | 2.6 | 66 | 80 |
| 4 | 2.8 | 65 | 75 |
| 5 | 3.0 | 62 | 80 |

4) The difference between alkyl aldehyde and aryl aldehyde: when the aldehyde is changed from aryl aldehyde (benzaldehyde) to alkyl aldehyde (propionaldehyde), the yields of carboxylic acid and ε-caprolactone are significantly reduced (Example 16, 21).

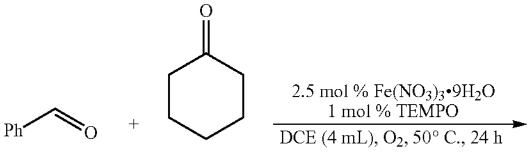

1f (2 mmol) 2 (1 mmol)

-continued

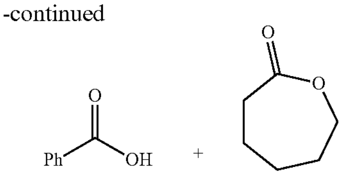
3f (54%) 4 (65%)

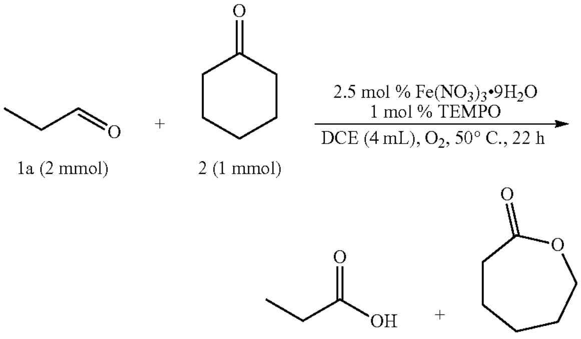

1a (2 mmol) 2 (1 mmol)
3a (43%) 4 (19%)

5) The effect of feeding mode change: the feeding mode is changed from one-time addition to slow dropping, the yields of carboxylic acid and ε-caprolactone are significantly improved (Examples 21, 22).

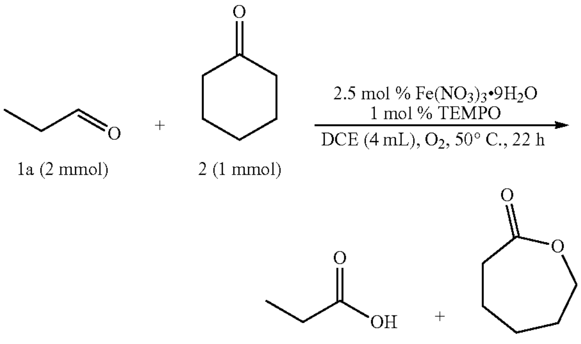

1a (2 mmol) 2 (1 mmol)
3a (43%) 4 (19%)

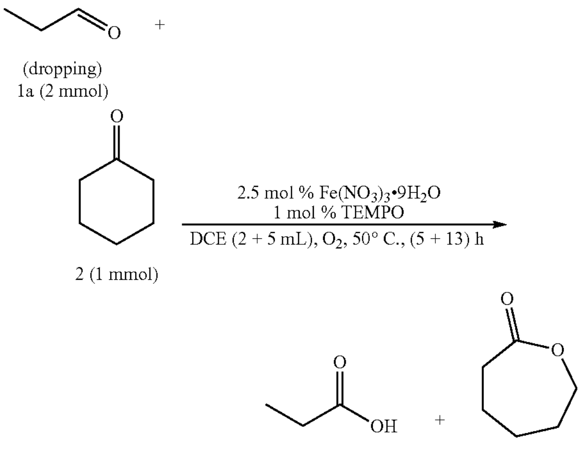

1a (2 mmol)
2 (1 mmol)
3a (92%) 4 (57%)

6) The effect of temperature change on the reaction: It should be pointed out that when the reaction is carried out by dropwise addition, the reaction only needs to add 2.5 mol % of ferric nitrate nonahydrate as a catalyst to obtain propionic acid and ε-caprolactone in a comparable yield. (Examples 23, 24); when the reaction temperature drops from 50° C. to 30° C., the reaction could still proceed, and both carboxylic acid and ε-caprolactone could be obtained in good to excellent yields (Example 24, 25).

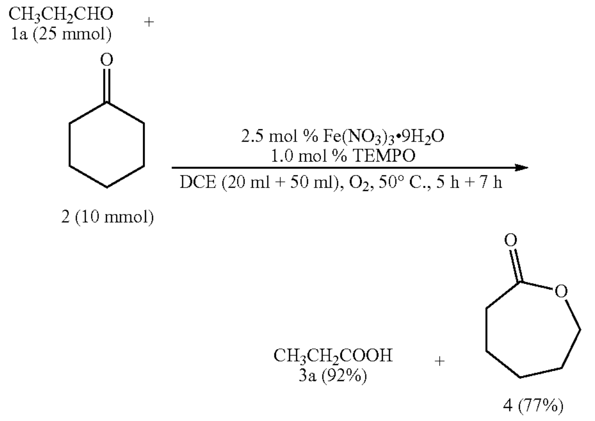

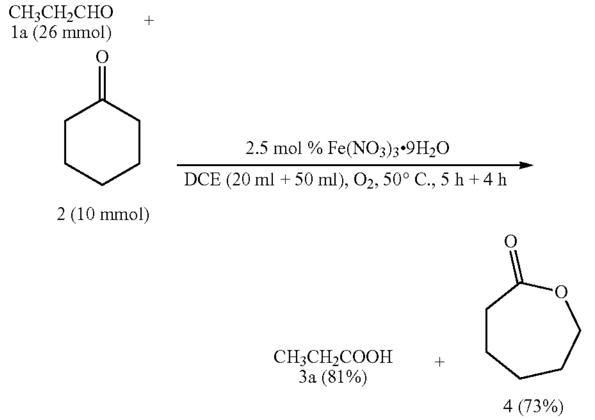

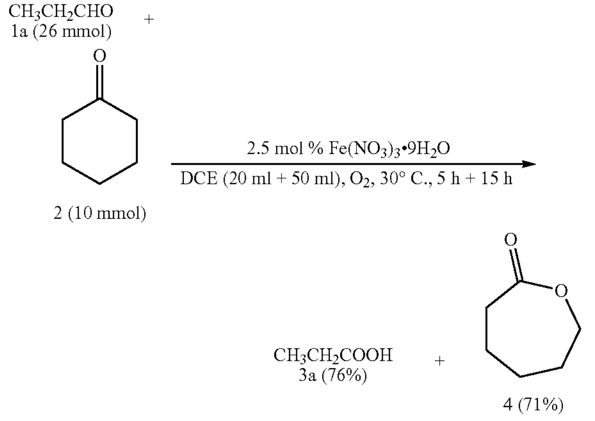

Finally, it should also be noted that the above enumeration is only a few specific embodiments of the present invention. Obviously, the present invention is not limited to the above embodiments, and many modifications are possible. All deformations that can be directly derived or associated by those skilled in the art from the contents disclosed in the invention should be considered as the protection scope of the invention.

What is claimed:

1. A method for co-production of carboxylic acid and ε-caprolactone based on aerobic oxidation, wherein, in the presence of oxygen, an aldehyde solution is added to a catalyst, organic solvent and cyclohexanone; the resulting mixture is stirred until the completion of the reaction, then the ε-caprolactone and carboxylic acid are obtained by column chromatography or distillation, and the reaction equation is shown in the following equation (A):

reaction equation(A)

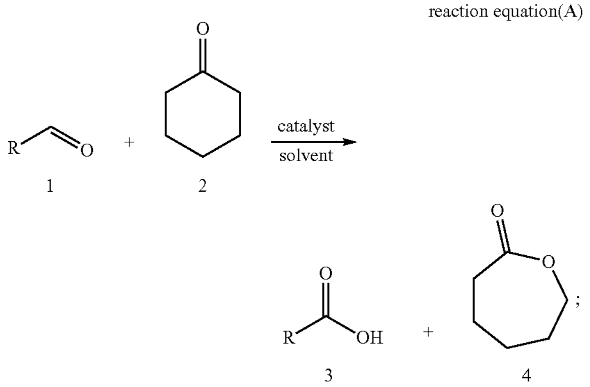

wherein, R is a C2-C4 linear or branched alkyl group;

the catalyst is selected from one or both of ferric nitrate nonahydrate and copper nitrate trihydrate;

a reaction temperature is from room temperature to 50° C.; and the molar ratio of the aldehyde, cyclohexanone and catalyst is 250~300:100:1~10.

2. The method of claim 1, wherein the catalyst further comprises 2,2,6,6-tetramethylpiperidine oxide; the molar ratio of the cyclohexanone and 2,2,6,6-tetramethylpiperidine oxide is 100:1~5.

3. The method of claim 1, wherein the solvent is selected from one or more of 1,2-dichloroethane, 1,1-dichloroethane, 1,2-dichloropropane, 1,3-dichloropropane and ethyl acetate.

4. The method of claim 1, wherein the addition method of the said aldehyde is one-time addition or dropwise addition.

5. The method of claim 1, wherein the oxygen is pure oxygen or oxygen in the air.

6. The method of claim 1, wherein the reaction time is 4-72 hours.

* * * * *